United States Patent [19]

Hanson

[11] Patent Number: 4,877,025

[45] Date of Patent: Oct. 31, 1989

[54] TRACHEOSTOMY TUBE VALVE APPARATUS

[76] Inventor: Donald W. Hanson, 8516 Great Plains Blvd., Chanhassen, Minn. 55317

[21] Appl. No.: 254,258

[22] Filed: Oct. 6, 1988

[51] Int. Cl.4 ............................................. A61M 16/00
[52] U.S. Cl. ........................... 128/207.16; 128/207.15; 128/912
[58] Field of Search ....................... 128/207.16, 207.15, 128/912, 346; 604/256, 53; 251/5

[56] References Cited

U.S. PATENT DOCUMENTS

| | | | |
|---|---|---|---|
| 3,137,299 | 6/1964 | Tabor | 128/207.16 |
| 3,469,582 | 9/1969 | Jackson | 251/5 |
| 3,538,917 | 11/1970 | Selker | 251/5 |
| 3,717,174 | 2/1973 | Dewall | 251/5 |
| 4,040,428 | 8/1977 | Clifford | 128/207.16 |
| 4,684,364 | 8/1987 | Sawyer et al. | 251/5 |
| 4,701,160 | 10/1987 | Lindsay et al. | 604/53 |

Primary Examiner—Edgar S. Burr
Assistant Examiner—Aaron J. Lewis
Attorney, Agent, or Firm—Clayton R. Johnson

[57] ABSTRACT

A fenestrated tracheostomy tube valve assembly removably insertable in a tracheostomy stoma and having an enlarged flange abuttable against the skin of the throat, a smaller diameter flange in the trachea and abuttable against the tissue surrounding the opening of the stoma to the trachea, a tube part extendable through the stoma and joined to said flanges, and an inflatable annular diaphragm joined to said flanges that extends through the tube part and in conjunction with the inner peripheral wall of the tube part forms an inflatable chamber. A squeeze ball is fluidly connected by a flexible fluid conduit to open through the enlarged flange to the inflatable chamber, and when the squeeze ball is squeezed, inflate the chamber to block fluid flow axially through the tube assembly and when the squeeze pressure is released, the chamber is deflated to permit fluid flow through said assembly to and from the trachea. Blocking fluid flow through the tube assembly facilitates speech.

16 Claims, 1 Drawing Sheet

TRACHEOSTOMY TUBE VALVE APPARATUS

BACKGROUND OF THE INVENTION

It is old to provide a tracheostomy tube that has an exterior flange with a band extended around the neck to hold the flange in place and a flap member mounted by the flange and is hand movable between a closed position blocking fluid flow through the tube when one desires to speak and an open position to permit breathing. This is a somewhat cumbersome procedure as is the case in the event a finger is used to close a tracheostomy stoma or a tube extending through a stoma.

Saul-4,538,607 discloses a tracheostomy valve connected to a permanent tracheostomy tube. A valve disc moves to a closed position by air pressure from the patient (closed speaking position shown in FIG. 2 of Saul). The disc is axially aligned with the tube proximal end such that when the air flows through the valve the air flow stream is reversely curved around the peripheral edge of the disc, and air flow is impeded. Capra-3,066,674 discloses an attachment for a throat tube that includes a ball valve arrangement which automatically closes when an individual begins to talk, but otherwise is open.

Liegner-4,459,984 discloses a thracheostomy tube and a pilot balloon pump to inflate or deflate a cuff to selectively form a fluid seal between the cannula body and the tracheal wall. Latham-4,280,492 discloses a trachesotomy tube having a U-shaped ventilator exterior of the neck, the ventilator including an outlet conduit leg with an inflatable valve therein. The valve is inflated when air is to flow into the trachea.

In order to provide an improved tracheostomy tube apparatus that facilitates speaking by a person having a tracheostomy stoma, this invention has been made.

SUMMARY OF THE INVENTION

A tracheostomy tube valve assembly is removably insertable into a tracheostomy stoma and has flanges for retaining the assembly in place while speaking and a tube part and a diaphragm in the tube part that cooperatively provide an inflatable chamber for blocking fluid flow through the tube part, and a manually squeezable ball in fluid communication with the chamber for controlling the inflation and deflation of the chamber.

One of the objects of this invention is to provide new and novel means for selectively blocking fluid flow through a tracheostomy stoma while a person is speaking and otherwise permit fluid flow therethrough. A further object of this invention is to provide a tracheostomy tube having new and novel means for removably retaining the tube in place in a tracheostomy stoma. Another object of this invention is to provide a tracheostomy stoma tube having new and novel means for controlling air flow through a tracheostomy stoma to facilitate speaking and when not blocking air flow, provide minimum impedance to airflow.

Figure 1:
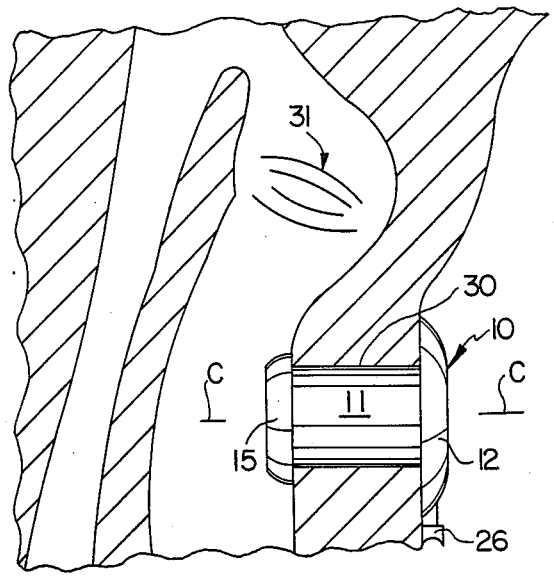
FIG. 1 is a pictorial showing, part in section, of the tracheostomy valve assembly of this invention in position for use.

The tracheostomy tube valve apparatus of this invention includes a tracheostomy tube valve assembly, generally designated 10, having a circumferential cylinder tube part 11, an exterior enlarged diametric (proximal) annular flange 12 joined to the proximal end of the tube part and an interior diametric (distal) annular flange 13 joined to the distal end of the tube part. The outer diameter of the distal flange is substantially greater than that of the outer diameter of the tube part but substantially less that that of the proximal flange. The assembly 10 also includes a tubular diaphragm portion 15 having one annular end joined to the proximal flange and an axial opposite annular end joined to a diaphragm flange 16. The central axes C—C of flanges 12, 13 and the tube part are coextensive.

Figure 4:
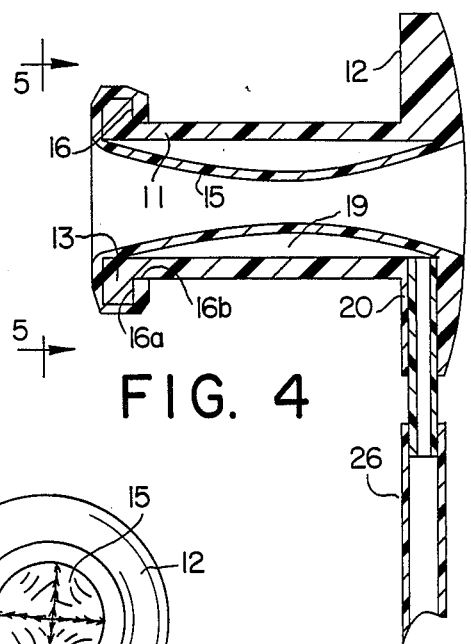
FIG. 4 is an elevated view of the assembly of FIG. 1 with the inflatable chamber partially inflated and the wall thickness of the diaphragm portion in the tube part interior being exaggerated.
Figure 5:
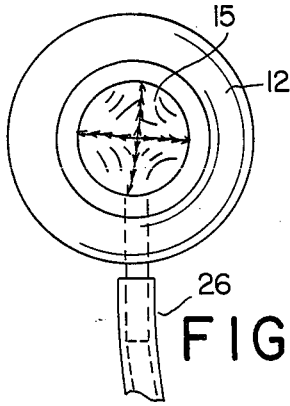
FIG. 5 is a distal end view of the tracheostomy valve assembly that is generally taken along the line and in the direction of the arrows 5—5 of FIG. 4, other than the inflatable chamber is fully inflated.
Figure 2:
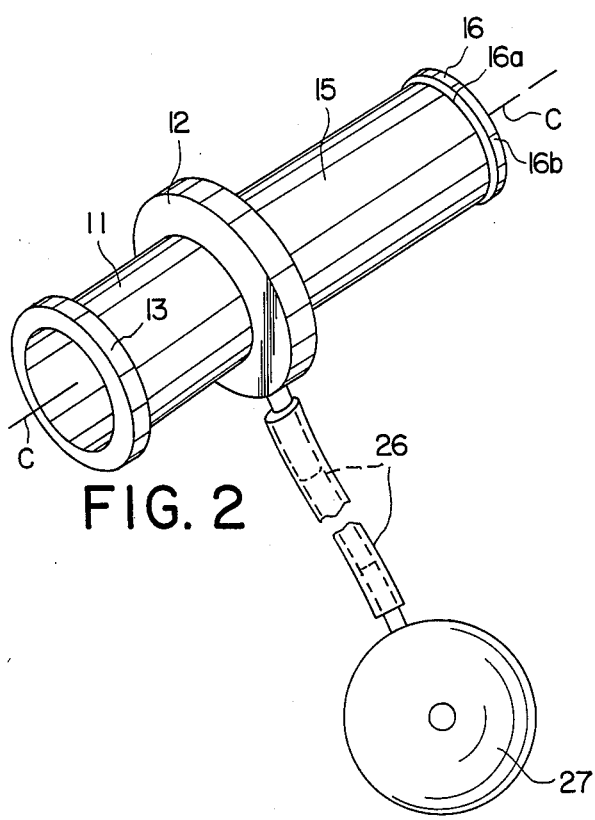
FIG. 2 is a perspective view of the valve assembly as moulded and also shows the squeeze ball and the conduit, with an intermediate part broken away, that fluidly connects the squeeze ball interior to the finished assembly.

Even though the assembly 10 may be made up of several individual parts that are suitably joined together to form the the the finished assembly of FIG. 4, advantageously the assembly may be moulded as a single unitary part such as illustrated in FIG. 2. The assembly part of FIG. 2 as moulded has members 11-13, 15 and 16 concentric to its central axis C—C with the tube diaphragm portion 15 axially between flanges 12, 16 and on the opposite side of flange 12 from the tube part 11. The tube part, flange 12 and diaphragm 15, 16 as moulded are of the same inner diameters while the outer diameter of the diaphragm portion 15 is less than that of the tube part such that the wall thickness of the diaphragm portion 15 is several times less than than that of the tube part and the outer diameter of the diaphragm flange 16 is less than that of the distal flange 13, greater than that of the diaphragm portion 15 and may be less than that of the tube part.

Figure 3:
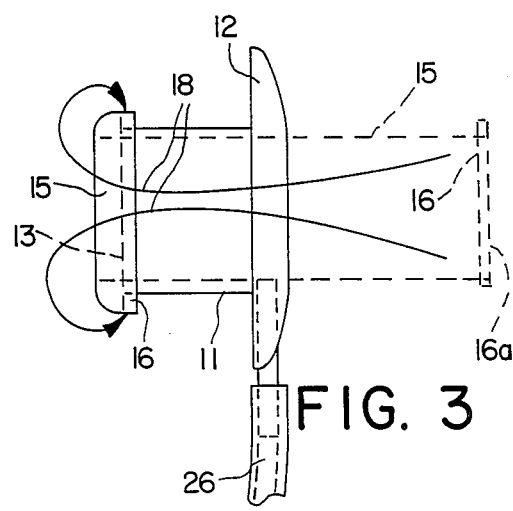
FIG. 3 is a diagrammatic indication of the manipulation of the moulded assembly to form the finished assembly with the diaphragm to the right of the distal flange prior to manipulation being shown in dotted lines while the arrows indicate the movement of the tube diaphragm into the tube part to form the inflatable chamber.

As indicated in FIG. 3, the diaphragm flange 16 is moved through the diaphragm portion 15 and the tube part in the direction of the arrows 18 and then rolled over the distal flange 13 whereby the terminal annular surface 16a of flange 16 abuts against the proximal annular surface of the distal flange 13 (other than for possibly an adhering compound), and the originally formed outer peripheral surface 16b of the flange 16 is radially closely adjacent to or abuts against the distal radial outer circumferential surface portion of the tube part. As a result the radial outer surface of the tube diaphragm portion 15 of the moulded assembly part of FIG. 2 when in the assembled (finished) condition of FIG. 4 throughout the major part of the axial length of the diaphragm is abuttable against the inner peripheral surface of the tube part. The flange 16 and/or the portion of the diaphragm portion 15 are suitably joined to the adjacent parts of the distal flange, for example by a suitable cement. Preferably the entire tube valve assembly is made of a resilient material such as a medical grade silicone rubber.

The tube diaphragm portion 15 is of a greater axial length than the tube part axially between flanges 12, 13 and of a length that portion 15 is stretched around its entire periphery axially between the juncture of the diaphragm portion 15 to flange 13 and the juncture of the diaphragm portion to flange 12. The diaphragm is joined to flanges 12, 13 to form an annular fluid chamber 19 that is sealed (closed), other than for the passage 20 that extends through the proximal flange 12 to permit the flow of fluid from and to the chamber.

An elongated flexible conduit 26, for example of a length to extend from the pocket in a pair of pants of the user to the tracheostomy stoma, has one end opening through passage 20 to open to the chamber 19 and an opposite end attached to a squeeze ball 27 to open to the interior of the squeeze ball which may be of a generally spherical or elliptical shape. The tube diaphragm is of a resiliency such that when the chamber 19 is in a non-inflated condition the diaphragm axially between the flanges has substantially its entire inner peripheral surface in abutting or very nearly in abutting relation to the entire inner peripheral surface of the tube part (valve fully open position) and when fully inflated, radially adjacent parts of the diaphragm portion are in abutting relationship so that fluid flow axially through the tube part is blocked (valve closed speaking position). The relative wall thicknesses of the tube part and the diaphragm portion 15 are such that when the chamber is inflated to the valve closed position, there is no significant bulging of the tube part. The ball and conduit in conjunction with the assembly parts defining chamber 19 form a closed system whereby when the ball is squeezed, the reduced interior volume of the ball forces fluid (air) into chamber 19 to fully inflate the chamber while when the squeezing pressure is released, to allow the ball to resiliently return to its datum condition, air is withdrawn from chamber 19 while the diaphragm also acts to force air out of the chamber. The interior volume of the ball is such that the chamber will not be overflated to burst the diaphragm by squeezing the ball.

The axial length of the tube part and the resiliency of the flanges are such that the flange 13 may be pushed in through the tracheostomy stoma 30 below the larynx 30 with the proximal flange forming a close or sealing fit with the skin of the neck surrounding the stoma and the distal flange forming a close or sealing fit with the tissue forming the trachea wall surrounding the opening of the stoma to the trachea. The distal and proximal flanges act to hold the assembly 10 in place during breathing and speaking; however permit the flange 13 being pulled through the stoma by grasping and pulling on the proximal flange. The outer diameter of the flange 13 and the part of the diaphragm extending radially outwardly thereof is greater than the stoma. As may be noted from FIG. 1, in a position of use the assembly 10 is not curved downwardly in the trachea as in the case with many conventional types of tracheostomy tube.

Even though the tube assembly has been described as having the diaphragm joined to the proximal flange, it is to be understood that the proximal flange may be considered as extending radially outwardly of the tube part proximal end circumferential surface and joined thereto, that the distal flange may be considered as being joined to the outer circumferential surface of the tube part to extend radially outwardly thereof and joined thereto, and that with the thus modified structure the diaphragm portion 15 would be integrally joined to the tube part proximal end. Further even though it is preferred that the diaphragm portion 15 extends axially the entire axial dimension between the distal and proximal flanges, the annular ends of the diaphragm may be joined to the appropriate ones of the distal and proximal flanges and the tube part to extend less than the entire length of the tube part, but at least the major part of the length of the tube part, provided that when the annular chamber is fully inflated, axial flow through the tube part and the flanges is blocked.

The outer diameter of the distal flange and the axial spacing of the flanges 13, 12 would at least in part depend upon the diameter and axial length of the tracheostomy stoma. Further the resiliency and dimensions of the flanges 13, 16 are such that these flanges may be manually pushed through the stoma and retained extending within the trachea during normal use, but still permit the flanges 13, 16 being manually pulled through the stoma when it is desired to remove the tube assembly from extending within the stoma. Additionally it is to be noted that when inserted in the stoma the axially opposite annular terminal surfaces of the tube assembly have coextensive central axes C—C and thus the tube assembly is not curved downwardly in the trachea as is the situation with most conventional tracheostomy tubes that I am aware of. The central axes of the assembly 10 and the stoma 30 are substantially coextensive in the position of use.

What is claimed is:

1. Tracheostomy tube valve apparatus insertable into tracheostomy stoma in the neck of a patient to extend through the tracheal wall into the trachea, comprising a tube valve assembly that includes a tube part having an inner peripheral wall, a distal annular end and a proximal annular end, a proximal annular flange adapted for abutment against the skin of the throat and being joined to the tube part proximal end, a distal annular flange insertable through the stoma and adapted for forming a close fit with the tissue surrounding the stoma being joined to the tube part distal end in axial spaced relation to the proximal flange, each flange being of an outer diameter substantially larger than the outer diameter of the tube part, and inflatable first means joined to at least one of the distal flange, the proximal flange and the tube part, and extending within the tube part between the flanges, for selectively being inflated to block fluid flow through the tube part and second means connected to the assembly for selectively inflating the inflatable means and deflating the inflatable means when the inflatable means is inflated, said inflatable first means includes means acting in cooperation with the inner peripheral wall for forming an inflatable chamber that when inflated blocks fluid flow through the tube part, and that the second means includes a fluid passage that opens through the proximal flange to the chamber to permit fluid flow to and from the chamber.

2. The apparatus of claim 1 wherein the stoma has a central axis, further characterized in that the assembly, including the flanges, has a central axis, that the assembly when inserted into the stoma has its central axis substantially aligned with the stoma central axis and that the distal flange is made of a larger outer diameter than the diameter of the stoma.

3. The apparatus of claim 1 further characterized in that means acting in cooperation with said inner peripheral wall comprises a flexible tube diaphragm that when the inflatable means is deflated permits air flow therethrough and through the tube part, the diaphragm having axial opposite annular proximal and distal ends.

4. The apparatus of claim 3 further characterized in that the diaphragm distal end is concentric to at least one of the distal flange and the tube part distal end and joined to at least one of the distal flange and tube part and that the diaphragm proximal end is concentric to at least of the tube part proximal end and the proximal flange and joined to at least one of the proximal flange and the tube part proximal end.

5. The apparatus of claim 4 further characterized in that the diaphragm and tube part inner peripheral wall defines an inflatable annular chamber and that the second means includes a squeeze ball and a fluid conduit connected to the squeeze ball and the assembly for forcing fluid to flow to inflate the annular chamber when the squeeze ball is squeezed and withdraw fluid from the inflated annular chamber when the squeezing pressure is released.

6. Tracheostomy tube valve apparatus insertable into a tracheostomy stoma to a position of use extending through the tracheal wall surrounding the stoma to the trachea for facilitating speaking, comprising a tube valve assembly that includes an axially extending tube part that is adapted for extending through the stoma and has an inner peripheral wall, a distal annular end and a proximal annular end, annular first means joined to the tube part for removably retaining the tube part in place in the stoma, axial extending annular second means that in coopertion with the tube part inner peripheral wall form an annular inflatable chamber that when inflated, blocks fluid flow through the tube part to facilitate speaking and when deflated permits fluid flow axially through the tube part, the second means having an inner peripheral annular surface defining a fluid passage through which fluid may flow to flow axially through the tube part when the inflatable chamber is at least partially deflated, and third means connected to the assembly for selectively forcing fluid to inflate the chamber and thereby to move the second means to block fluid flow through the tube part and alternately conducting fluid out of the chamber to deflate the chamber and permit the flow of fluid through the tube part, said first means includes a proximal flange joined to the tube part proximal annular end that is of a larger outer diameter than the tube part and has a fluid passage extending therein that opens to the chamber and that the third means is connected to the proximal flange for forcing fluid through the passage and alternatively conducting fluid away from the chamber.

7. The apparatus of claim 6 further characterized in that when the assembly is inserted into the stoma in a position of use, the tube part and the second means are substantially coaxially aligned, and that the second means has a portion that extends within the tube part at least a major part of the axial distance between the tube ends.

8. The apparatus of claim 6 further characterized in that the first means includes a distal annular flange joined to the tube part distal end that is of an outer diameter larger than the outer diameter of the tube part and the diameter of the stoma and is made of a resilient material.

9. The apparatus of claim 8 further characterized in that the distal flange has an outer peripheral surface and that the second means comprises a resilient tube diaphragm having an annular wall portion of a wall thickness many times less than the wall thickness of the tube part, extending axially within the tube part, and also extends in contact with the flange outer peripheral surface.

10. The apparatus of claim 6 further characterized in that the second means comprises an axially elongated, resilient diaphragm extending generally concentrically within the tube part in the second means deflated condition.

11. The apparatus of claim 10 further characterized in that the first means comprises a distal annular flange joined to the tube part distal end, the flanges, diaphragm and tube part having axial opposite annular distal and proximal end portions, the diaphragm distal end portion being joined to at least one of the distal flange and the tube part distal end and the diaphragm proximal end being joined to at least one of the proximal flange and the tube part proximal end whereby the diaphragm axially between the tube part ends is in tension even when the chamber is deflated.

12. The apparatus of claim 11 further characterized in that each of the flanges are of substantially larger outer diameters than the tube part outer diameter, that the proximal flange outer diamter and that the third means comprises a squeeze ball and a fluid conduit in fluid communication with the squeeze ball that opens through the proximal flange to the fluid chamber to inflate the chamber when the squeese ball is subjected to squeezing pressure and result in deflation of the chamber when the squeezing pressure is released.

13. The apparatus of claim 10 further characterized in that the tube assembly is made of a medical grade silicone rubber, that the diaphragm comprises an axially elongated portion having a first annular end joined to the proximal flange and a second annular end and a diaphragm flange joined to the diaphragm second end and being of a smaller radial wall thickness than the distal flange radial wall thickness, the flanges, tube part and diaphragm portion being formed as a single unitary part.

14. The apparatus of claim 6 further characterized in that the second means includes a tubular diaphragm having one axial end portion axially and radially adjacent to the proximal flange and an opposite end portion axially and radially adjacent to the distal flange.

15. The apparatus of claim 11 further characterized in that when the inflatable means is inflated, the diaphragm in combination with the tube part form the annular chamber that opens to the proximal flange and that the third means includes a fluid conduit connected to the proximal flange that opens through the proximal flange to the chamber.

16. The apparatus of claim 15 further characterized in that the third means includes a squeeze ball connected to the conduit to inflate the chamber when squeezed and to withdraw fluid from the chamber when the squeezing pressure is released.

* * * * *